(12) United States Patent
Hayes (10) Patent No.: US 11,357,570 B2
(45) Date of Patent: Jun. 14, 2022

(54) ABLATION CATHETER WITH FIBER BRAGG GRATING STRAIN SENSORS

(71) Applicant: Lake Region Manufacturing, Inc., Chaska, MN (US)

(72) Inventor: John Michael Hayes, Cork (IE)

(73) Assignee: Lake Region Manufacturing, Inc., Chaska, MN (US)

( * ) Notice: Subject to any disclaimer, the term of this patent is extended or adjusted under 35 U.S.C. 154(b) by 90 days.

(21) Appl. No.: 16/851,764

(22) Filed: Apr. 17, 2020

(65) Prior Publication Data

US 2020/0330158 A1   Oct. 22, 2020

Related U.S. Application Data

(60) Provisional application No. 62/836,225, filed on Apr. 19, 2019.

(51) Int. Cl.
| | |
|---|---|
| *A61B 18/24* | (2006.01) |
| *A61B 34/20* | (2016.01) |
| *A61B 17/00* | (2006.01) |
| *A61B 18/00* | (2006.01) |

(52) U.S. Cl.
CPC .... *A61B 18/24* (2013.01); *A61B 2017/00862* (2013.01); *A61B 2018/00351* (2013.01); *A61B 2018/00577* (2013.01); *A61B 2034/2061* (2016.02)

(58) Field of Classification Search
CPC .......... A61B 18/24; A61B 2017/00862; A61B 2018/00351; A61B 2018/00577; A61B 2034/2061; A61B 34/71; A61B 2017/00327; A61B 2018/00357; A61B 5/6885; A61B 2018/00791; A61B 2090/064; A61B 2090/065; A61B 18/1492

See application file for complete search history.

(56) References Cited

U.S. PATENT DOCUMENTS

| | | |
|---|---|---|
| 7,497,853 B2 | 3/2009 | Fischer et al. |
| 7,553,305 B2 | 6/2009 | Honebrink et al. |
| 7,588,555 B2 | 9/2009 | Pudelko et al. |
| 7,615,044 B2 | 11/2009 | Scheibe et al. |
| D612,044 S | 3/2010 | Scheibe |
| D638,934 S | 5/2011 | Kimmel |
| 7,955,314 B2 | 6/2011 | Fischer et al. |
| 8,007,463 B2 | 8/2011 | Pudelko et al. |
| 8,048,026 B2 | 11/2011 | Fischer et al. |
| 8,048,063 B2 | 11/2011 | Aeby et al. |
| 8,056,207 B2 | 11/2011 | Honebrink et al. |
| D653,335 S | 1/2012 | Kampa et al. |
| D653,337 S | 1/2012 | Kampa et al. |
| 8,308,659 B2 | 11/2012 | Scheibe et al. |

(Continued)

*Primary Examiner* — Joseph M Dietrich
*Assistant Examiner* — Michael T. Holtzclaw
(74) *Attorney, Agent, or Firm* — Michael F. Scalise (57) ABSTRACT

An ablation catheter for treating cardiac arrhythmias by ablating near pulmonary venous tissue is described. The ablation catheter includes a system of optical fibers containing respective fiber Bragg gratings (FBG) that are susceptible to changes in strain to thereby indicate to the physician the amount of force that the ablation head is exerting on the myocardial tissue during the ablation procedure. Optionally, the FBGs are used to indicate the exact orientation of the catheter and its ablation head inside the vasculature.

19 Claims, 6 Drawing Sheets

(56) References Cited

U.S. PATENT DOCUMENTS

| | | |
|---|---|---|
| 8,444,626 B2 | 5/2013 | Fischer et al. |
| 8,540,697 B2 | 9/2013 | Honebrink et al. |
| 8,790,362 B1 | 7/2014 | Kimmel et al. |
| 9,149,607 B2 | 10/2015 | Scheibe et al. |
| 2009/0177095 A1 | 7/2009 | Aeby et al. |
| 2016/0128768 A1* | 5/2016 | Leo ................ A61B 18/1492 606/41 |
| 2017/0196479 A1* | 7/2017 | Liu .................... A61B 5/0245 |
| 2018/0085158 A1 | 3/2018 | Aeby |
| 2018/0154129 A1 | 6/2018 | Paul et al. |
| 2018/0206937 A1 | 7/2018 | Leo et al. |
| 2018/0339134 A1* | 11/2018 | Leo .................... A61B 5/0084 |
| 2019/0038228 A1* | 2/2019 | Daly ...................... G01K 7/02 |
| 2019/0374282 A1* | 12/2019 | Tegg ................ A61B 18/1477 |
| 2020/0238051 A1* | 7/2020 | Hwang ............... A61B 5/0084 |
| 2021/0052320 A1* | 2/2021 | Holmberg ........... A61B 5/6885 |

\* cited by examiner

ABLATION CATHETER WITH FIBER BRAGG GRATING STRAIN SENSORS

CROSS REFERENCE TO RELATED APPLICATION

This application claims priority to U.S. Provisional Application Ser. No. 62/836,225, filed on Apr. 19, 2019.

BACKGROUND OF THE INVENTION

1. Field of the Invention

The present invention relates to the field of medical devices, and specifically to catheters for conducting ablation therapy within myocardial tissue. More specifically, the present invention relates to ablation catheters for treating cardiac arrhythmias by ablating near pulmonary venous tissues. The ablation catheters include a system of optical fibers containing respective fiber Bragg gratings (FBG) that are susceptible to changes in strain to thereby indicate to the physician the amount of force that the ablation head is exerting on the myocardial tissue during the ablation procedure. Optionally, the FBGs are used to indicate the exact orientation of the catheter and its ablation head inside the vasculature.

2. Prior Art

The human heart routinely experiences electrical impulses traversing its many surfaces and ventricles, including the left atrium. Just prior to each heart contraction, the heart depolarizes and repolarizes as electrical currents spread across the heart and throughout the body. In healthy hearts, the surfaces and ventricles of the heart experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist because of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. These conditions are associated with a variety of ailments, including death.

Catheters are used in a variety of diagnostic and therapeutic medical procedures to diagnose and correct conditions such as atrial arrhythmia, including for example, ectopic atrial tachycardia, atrial fibrillation, and atrial flutter. Typically, in such a procedure, a catheter carrying one or more electrodes is moved through a patient's vasculature to the heart under fluoroscopy-guided observation. The electrodes may be used for mapping, ablation, diagnosis, or other treatments.

When an ablation therapy is desired to alleviate symptoms including atrial arrhythmia, the ablation catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that lead to arrhythmias. The ablation catheter may utilize ablative energy including, for example, radio-frequency (RF), cryoablation, laser, chemical, and high-intensity focused ultrasound.

Ablation therapies are often delivered by making a number of individual ablations in a controlled fashion in order to form a lesion line. To improve conformity of the individual ablations along the lesion line, it is desirable to precisely control the orientation of the catheter and its ablation head when the individual ablations are conducted, the contact force between the ablation head and the targeted tissue, and the ablation period. Thus, ablation therapies require accurate positioning of the ablation catheter as well as precise pressure exertion for optimal ablative-energy transfer into the targeted myocardial tissue. Inaccurate positioning of the ablation head in the myocardia may result in suboptimum ablation or inadvertent ablation of healthy tissue. Excess force between the ablation catheter head and the targeted myocardial tissue may result in excessive ablation, which may permanently damage cardiac muscle and surrounding nerves. On the other hand, when the contact force between the ablation head and the targeted myocardial tissue is below a target force, the efficacy of the ablation therapy may be reduced.

An ablation catheter marketed by St. Jude Medical GVA Sàrl as the TactiCath Quartz® catheter is described in U.S. Pat. No. 8,048,063 to Aeby et al. This catheter has a flexible elongated body including a tri-axial force sensor having a plurality of optical fibers connected to a housing. The housing includes a plurality of mirrored surfaces. The optical fibers are disposed relative to the housing to detect light intensity changes resulting from longitudinal and radial deformations of the housing. A controller receives an output from the optical fibers and computes a multi-dimensional force vector corresponding to the contact force of an RF ablation electrode mounted to the housing against myocardial tissue.

However, the TactiCath Quartz® catheter lacks a system for precisely controlling the orientation of the ablation head in the myocardial tissue. For a successful outcome, it is not enough to precisely control the applied force of the ablation head against myocardial tissue under conventional fluoroscopy-guided observation for locational accuracy. Instead, it is important to precisely control both the force exerted by the ablation head against the myocardial tissue and the orientation of the ablation catheter in the myocardium. Both are required.

Therefore, there is a need for an improved ablation catheter that is suitable for performing various diagnostic and therapeutic medical procedures to diagnose and correct conditions such as atrial arrhythmia where both the orientation of the catheter in the vasculature and the force exerted by the ablation head against the myocardial tissue are precisely controlled. The present ablation catheter provides these advantages.

SUMMARY OF THE INVENTION

There are two very important aspects of the present invention. First, the ablation catheter improves the efficacy of ablation therapy by more effectively maintaining a consistent force of the ablation head against the myocardial tissue being ablated during a single-point ablation, as well as along a lesion line comprising many individual ablations. Moreover, ablation therapy efficacy is improved using the directional accuracy of the present ablation catheter to navigate through the right atrium and to feedback to the user precise information regarding the amount of force the ablation head is exerting against myocardial tissue. Importantly, orientational accuracy inside the patient's body and the amount of force exerted by the ablation head on myocardial tissue are consistent throughout a cardiac ablation procedure, and the like.

In summary, the ablation catheter of the present invention includes a hypotube connected between the distal end of a catheter body and an ablation head. At least two optical fibers supported by the catheter body extend into the hypotube. Each optical fiber comprises a strain-sensing fiber Bragg grating (FBG) with a Bragg wavelength. A collar/collet assembly is disposed between an annular spring of the hypotube and the strain-sensing FBGs. A light source optically connected to the optical fibers emits light into the strain-sensing FBGs. Importantly, the emitted light spectrums are broad enough to cover all possible reflection spectrum of the FBGs due to strain and temperature variations imparted to them. Light wavelength detectors are optically connected to the at least two optical fibers, and a controller is operatively coupled to the first and second light wavelength detectors.

In use, the light source emits light of a first spectrum into the first FBG and light of a second spectrum into the second FBG. The FBGs reflect light of a Bragg wavelength in a first state when no axial force is imparted to the ablation head. However, in the case where there is an axial force, the ablation head assumes an unarticulated orientation, axially aligned with the catheter body. In this orientation, the collar/collet assembly applies equal radial pressure to the strain-sensing FBGs so that the respective reflected Bragg wavelengths received by their wavelength detectors are in a second state, shifted a similar amount with respect to the first state. A controller optically connected to the optical fibers then calculates the magnitude of the axial force vector imparted to the ablation head.

Moreover, when a lateral force causes the ablation head to deflect out of axial alignment with the catheter body, the spring of the hypotube is also deflected. This causes the collar/collet assembly to apply a greater lateral force to one of the FBGs than to the other. In comparison to when the FBGs reflect light having Bragg wavelengths that are in the first state without any axial force being imparted to the ablation head, the reflected Bragg wavelengths are in respective lateral force induced states. The lateral force induced states of the FBGs are converted by the controller into information related to the lateral force vector that is imparted to the ablation head. The lateral force vector is related to the precise pressure being exerted by the ablation head against the targeted myocardial tissue and in turn the ablative-energy being transferred into the myocardial tissue.

Thus, the controller is programmed to calculate both axial and lateral forces imparted to the ablation head. This means that the actual force vector imparted to the ablation head is the lateral force vector added to the axial force vector.

Further embodiments of ablation catheters according to the present invention include push-pull wires extending from a handle assembly connected to a proximal end of the catheter body to the ablation head. Manipulation of the handle assembly moves the push-pull wires to selectively deflect the ablation head. In addition to being programmed to determine the amount of force that the ablation head is exerting against myocardial tissue, the controller is programmed to use the axial and lateral force induced states of the FBGs to determine an exact orientational value of the ablation head out of axial alignment with the catheter body. In this embodiment, the orientation of the ablation head caused by manipulation of the pull wires is first ascertained and then when the ablation head is pressed against myocardial tissue, any added change in the Bragg wavelengths is used to calculate the additional force vector resulting from contact with myocardial tissue.

These and other aspects of the present invention will become increasingly more apparent to those skilled in the art by reference to the following detailed description and to the appended drawings.

DETAILED DESCRIPTION OF THE PREFERRED EMBODIMENTS

Figure 1:
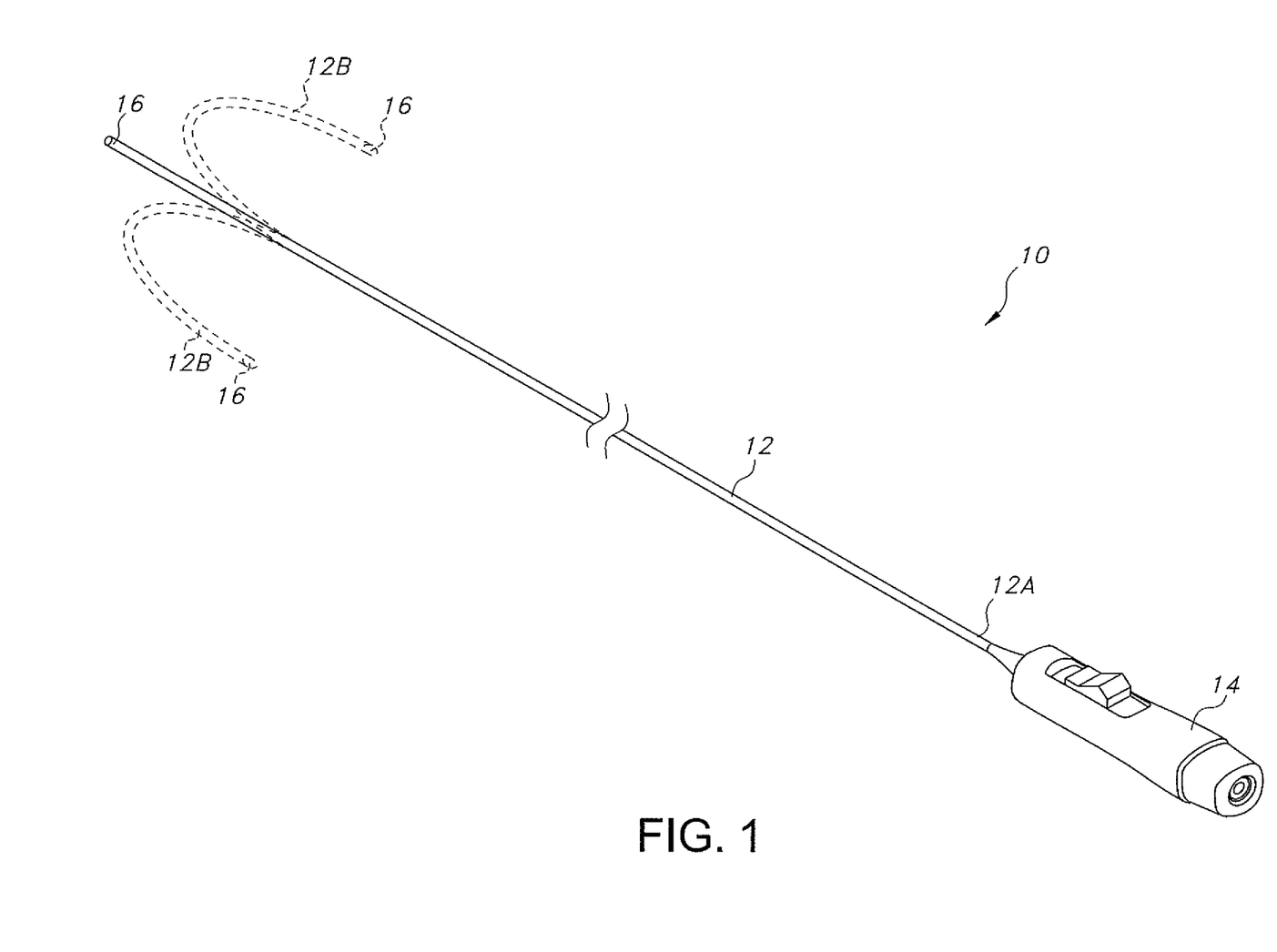
FIG. 1 is a schematic view of an ablation catheter 10 according to the present invention.

Turning now to the drawings, FIG. 1 illustrates an exemplary ablation catheter 10 according to the present invention. The ablation catheter 10 includes a catheter body 12 which, as an elongate tubular structure, is flexible yet substantially non-compressible along its length. The catheter body 12 connects between a handle assembly 14 and a distal ablation head 16. In one embodiment, the handle assembly 14 houses a steering and locking mechanism that provides for selective deflection or steering of the catheter body 12 and its ablation head 16 into any number of disparate orientations within the vasculature of a patient and then for locking the catheter body in a desired orientation for performing a medical procedure. FIG. 1 illustrates the catheter body 12 in two generally opposed articulated orientations (depicted in dashed lines) and an unarticulated neutral orientation. In another embodiment, the ablation catheter 10 does not have structure for selective deflection or steering of the catheter body 12 and its ablation head 16.

For a more thorough understanding of catheter handles that are useful with the present invention, reference is made to U.S. Design Pat. Nos. D612,044 to Scheibe, D638,934 to Kimmel, D653,335 to Kampa et al. and D653,337 to Kampa et al., all of which are assigned to the assignee of the present invention and incorporated herein by reference.

For a more thorough understanding of deflectable catheter steering and locking systems that are useful with the present invention, reference is made to U.S. Pat. No. 7,497,853 to Fischer et al., U.S. Pat. No. 7,588,555 to Pudelko et al., U.S. Pat. No. 7,615,044 to Scheibe et al., U.S. Pat. No. 7,955,314 to Fischer et al., U.S. Pat. No. 8,007,463 to Pudelko et al., U.S. Pat. No. 8,048,026 to Fischer et al., U.S. Pat. No. 8,308,659 to Scheibe et al., U.S. Pat. No. 8,444,626 to Fischer et al., U.S. Pat. No. 8,790,362 to Kimmel et al. and U.S. Pat. No. 9,149,607 to Scheibe et al., all of which are assigned to the assignee of the present invention and incorporated herein by reference.

An exemplary catheter body 12 is a tubular member having a delivery lumen 18 (FIGS. 2 and 3D) that extends from a catheter proximal portion 12A (FIG. 1) received in the handle assembly 14 to a distal portion 12B connected to the ablation head 16. The tubular body 12 is formed of a polymeric material, such as of PEBAX, encasing a tubular wire braided as a mesh. A liner of a second polymeric material, for example PTFE, resides inside the PEBAX tube. The PTFE liner provides the delivery lumen 18 with sufficient lubricity so that medical instruments, devices, and the like, slide through the lumen with a minimal amount of force. The delivery lumen 18 is sized and shaped to receive, for example, instruments, fluids, media, and the like.

FIGS. 2 and 3A to 3D show that the ablation head 16 connected to the distal portion 12B of the catheter body 12 has a cylindrically-shaped body 20 extending axially from a proximal sleeve portion 22 to a distal atraumatic tip 24. A stepped intermediate portion 26 resides between and connects to the proximal sleeve 22 and the distal tip 24. A main lumen 28 extends axially along the proximal sleeve 22, through the intermediate ablation head portion 26 and into the atraumatic tip 24. This lumen 28 is in open communication with the delivery lumen 18 extending through the tubular catheter body 12. Suitable materials for the ablation head 16 include stainless steel, nickel, titanium, platinum, and platinum iridium.

Part-way through the ablation head 16, the main lumen 28 steps down to a secondary axial lumen 30 that leads to the apex of the atraumatic tip 24. A plurality of lateral lumens 32 extend radially outwardly from the main lumen 28 to a cylindrical portion 24A of the atraumatic tip 24. While two lateral lumens 32 are shown in FIGS. 2, 3A, 3C and 3D, it is within the scope of the present invention that a plurality of lateral lumens can communicate laterally between and to the main lumen 28 and the outer surface 24B of the atraumatic tip 24. Preferably the lateral lumens 32 are evenly spaced about the circumference of the ablation head 16. For example, in an embodiment with four lateral lumens 32, the lumens are evenly spaced at 90° intervals from each other. In an embodiment with three lumens 32, the lateral lumens are evenly spaced 120° from each other.

FIGS. 2, 3A, 3C and 3D further show that in the selectively manipulatable embodiment, the deflectable ablation catheter 10 of the present invention has a push-pull wire 34 anchored to the distal ablation head 16. The push-pull wire 34 extends proximally from the ablation head 16 to the handle assembly 14. The handle assembly 14 enables a user to selectively manipulate the push-pull wire 34 in a forward or distal direction or in a backwards or proximal direction. That is for selectively deflecting the ablation head 16 in a myriad of orientations out of axial alignment as shown in FIG. 1. While only one push-pull wire 34 is depicted in FIGS. 2, 3A, 3C and 3D, it is understood that is by way of example only. A typical push-pull wire system has four push-pull wires 34 evenly spaced at 90° intervals about the circumference of the ablation head 16. Moreover, an anchor (not shown) couples a distal end of the push-pull wire 34 to a step 36 where the proximal sleeve 22 meets the intermediate ablation head portion 26.

For a more thorough understanding of push-pull wire systems including their anchoring mechanisms that are useful with the present invention, reference is made to U.S. Pat. Nos. 7,553,305, 8,056,207 and 8,540,697, all to Honebrink et al. and all of which are assigned to the assignee of the present invention and incorporated herein by reference. And, for a more thorough understanding of an anchor for a push-pull wire system, reference is made to U.S. Pat. No. 7,497,853 to Fischer et al., which is assigned to the assignee of the present invention and incorporated herein by reference.

FIGS. 2, 3A, 3C, 3D and 4 also depict a power cable 35 that is electrically connected to the ablation head 16. The power cable 35 extends proximally from the ablation head 16 to the handle assembly 14. There, it is configured for electrical connection to a power source for energizing the ablation head 16 during a medical procedure. To ablate tissue, the ablation head 16 is configured to electrically conduct a DC energy current or a radio-frequency energy into the targeted tissue. The ablation catheter 10 of the present invention can also be configured for cryoablation, laser ablation, chemical ablation, and ultrasonic ablation of a target tissue. In other embodiments, the cable 35 is used to provide electrical power to mapping electrodes (not shown), and the like, supported by the ablation head 16.

FIGS. 2, 3A, 3C and 3D further show that the ablation catheter 10 has an optical fiber 38 anchored to the step 36 where the proximal sleeve 22 meets the intermediate portion 26 of the ablation head 16. In one embodiment, there are two optical fibers 38 anchored to the ablation head 16. Preferably, the optical fibers 38 are diametrically opposed to each other inside a hypotube 44, which will be described in detail hereinafter. In another embodiment, there are three or more optical fibers 38 anchored to the ablation head 16. In any event, the optical fibers 38 are evenly spaced from each other inside the hypotube 44. Regardless the number, the optical fibers 38 extend proximally from the ablation head 16 to the handle assembly 14 and each contains a distal strain-sensing fiber Bragg grating (FBG) 40. However, only one of the two, three, or more optical fibers 38 contains a proximal temperature-sensing FBG 42. The first, second and third strain-sensing FBGs 40A to 40C and the temperature-sensing FBG 42 are individually selected from a phase-shifted FBG, a long-period FBG, an apodized FBG, a chirped FBGs, and a tilted FBG.

Figure 2:
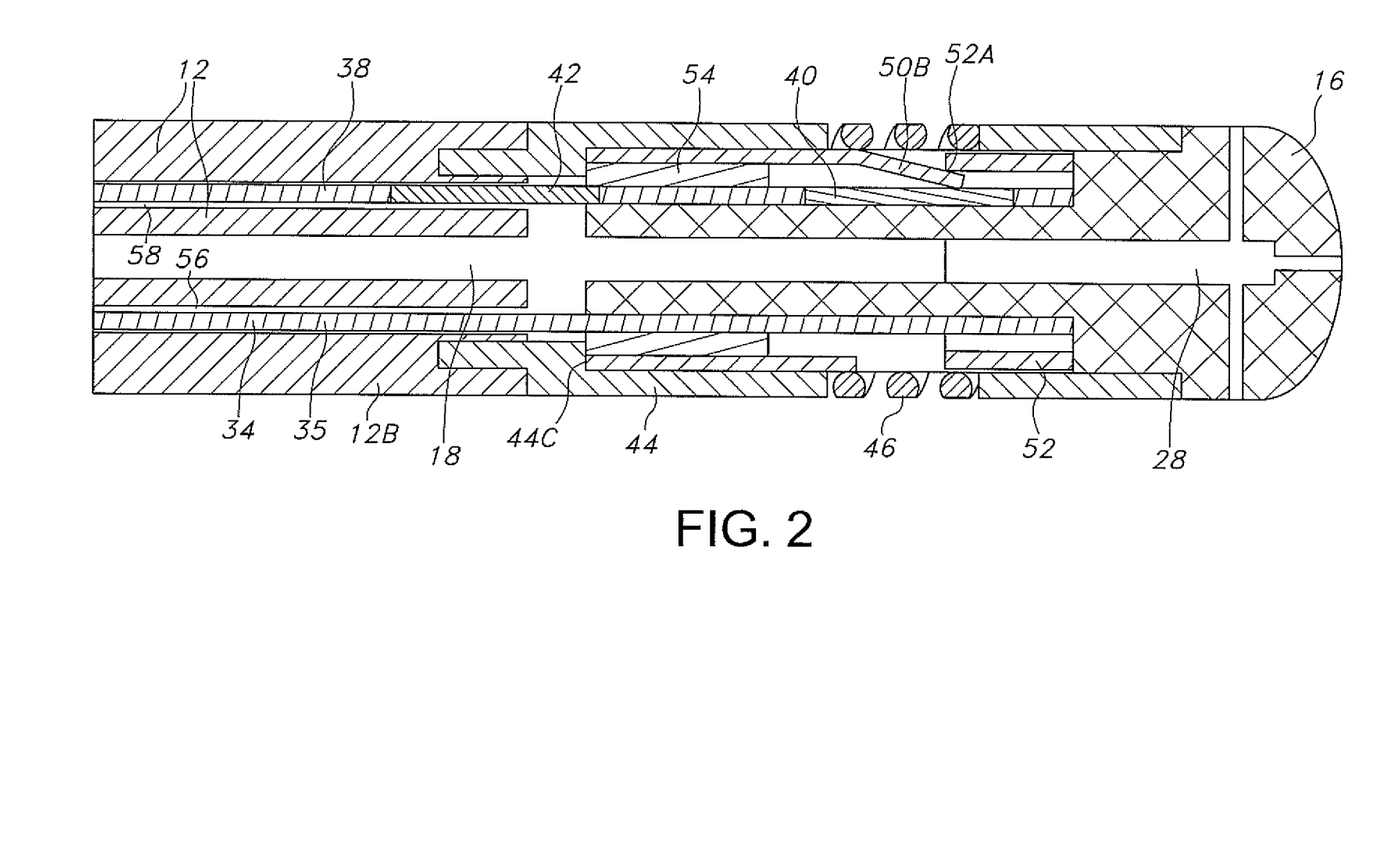
FIG. 2 is a partial cross-sectional view of an ablation head 16 connected to the distal portion 12B of a catheter body 12 of the ablation catheter 10 shown in FIG. 1.
Figures 3A, 3B:
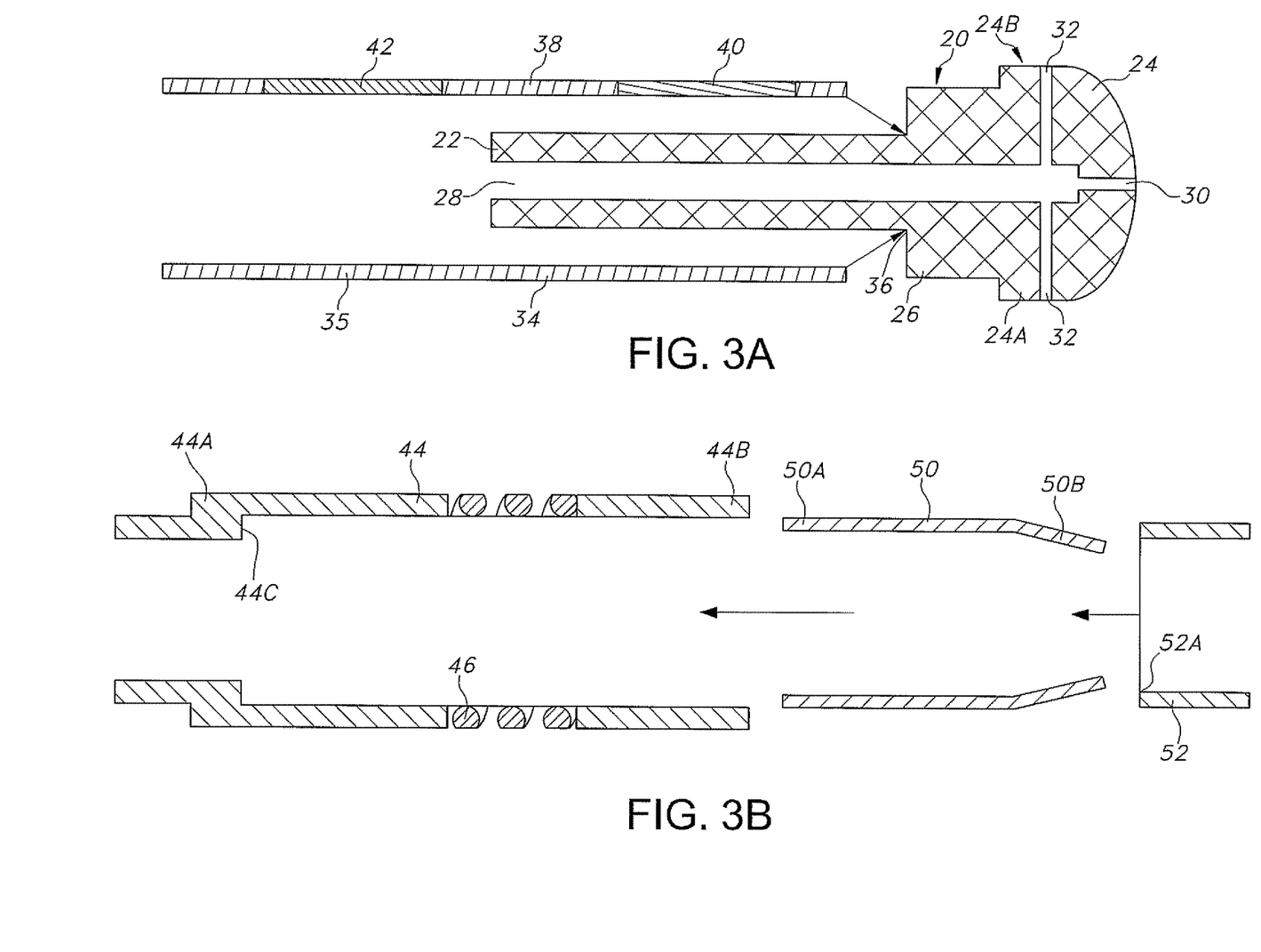
FIG. 3A is a partial cross-sectional view depicting an optical fiber 38 and a push-pull wire 34/power cable 35 being connected to the ablation head 16 shown in FIG. 2.
FIG. 3B is a partial cross-sectional view showing a hypotube 44 being connected to a collet 50 and a collar 52 prior to this subassembly being connected to the ablation head 16.
Figure 3C:
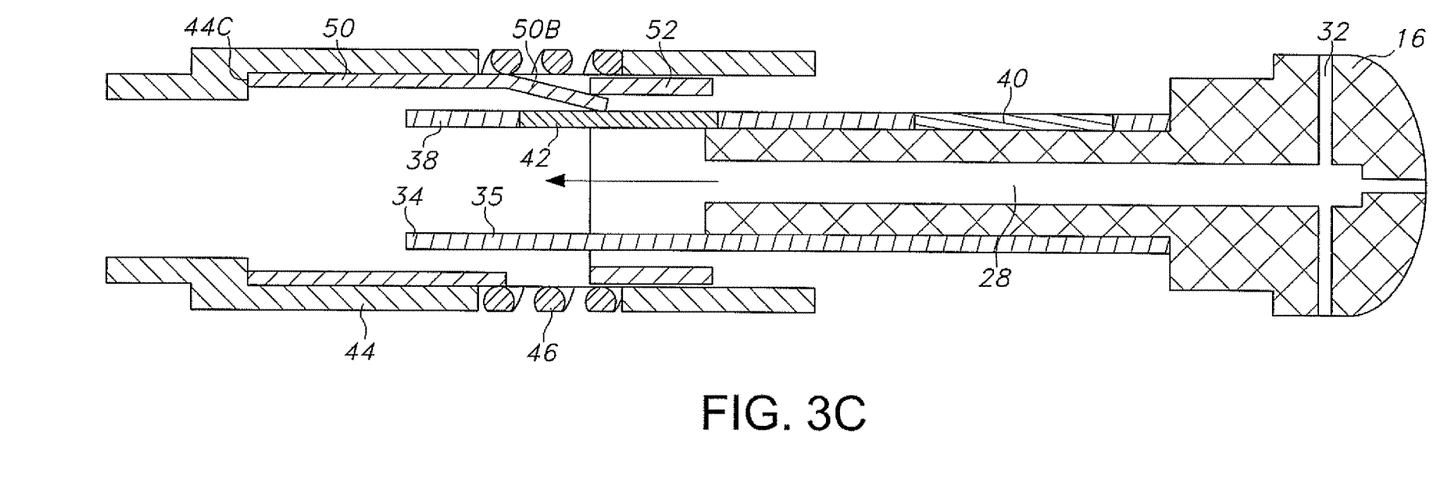
FIG. 3C is a partial cross-sectional view showing the hypotube 44, collet 50/collar 52 assembly being connected to the ablation head 16 including the push-pull wire 34/power cable 35 subassembly shown in FIG. 3A.
Figure 3D:
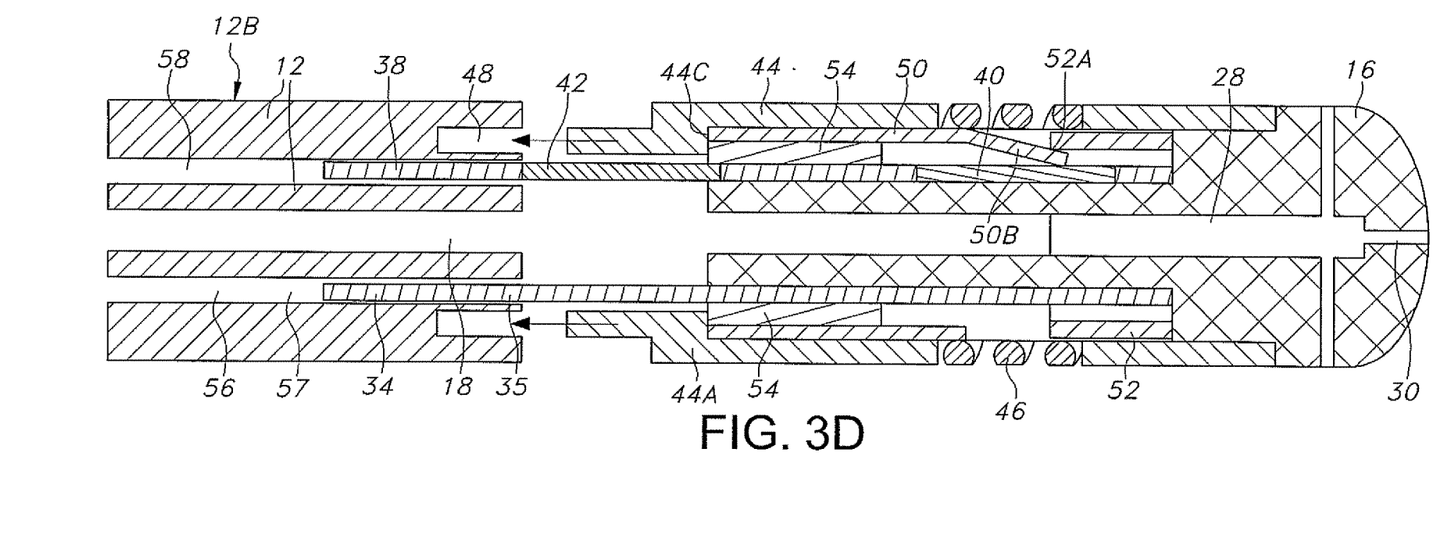
FIG. 3D is a partial cross-sectional view showing the ablation head 16 of FIG. 3C being connected to the distal portion 12b of the catheter body 12.
Figures 4, 6:
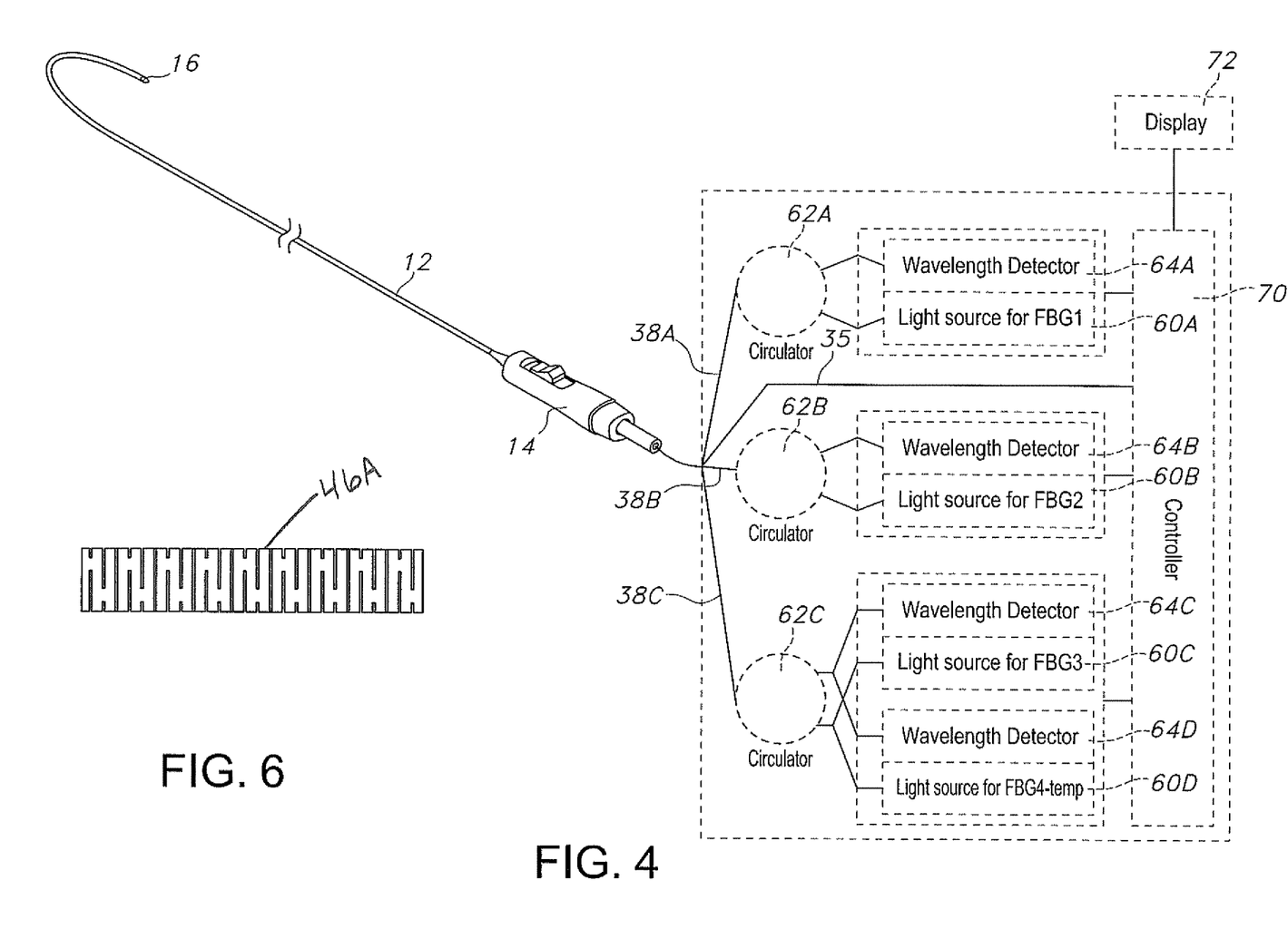
FIG. 4 is a schematic of the ablation catheter 10 shown in FIG. 1 including its three optical fibers 38A to 38C optically connected to respective light sources 60A to 60D and wavelength detectors 64A to 64D. A light source 60D and wavelength detector 64D for a temperature-sensing FBG 42 is also depicted.
FIG. 6 illustrates a slotted spring 46A that is useful with the hypotube 44 shown in FIGS. 2, 3B, 3C and 3D.

FIGS. 3B to 3D illustrate the steps for constructing the distal portion of the ablation catheter 10 shown in FIG. 2. The ablation head 16 comprises the hypotube 44 extending from a stepped proximal portion 44A to a cylindrically-shaped distal portion 44B. A spring is cut into or otherwise provided in the hypotube 44 at an intermediate location between the proximal and distal portions 44A, 44B. FIGS. 2, 3A, 30 and 3D illustrate the spring as a coil spring 46. Alternately, FIG. 6 shows the spring as a slotted spring 46A.

The stepped proximal portion 44A of the hypotube 44 is received in an annular groove 48 (FIG. 3D) that extends proximally a relatively short distance from a distal face of the catheter body 12. With the hypotube 44 secured to the catheter body 12, their respective outer surfaces have substantially similar outer diameters aligned with each other. Suitable materials for the hypotube 44 include stainless steel, nickel, titanium, platinum, platinum iridium, and a medical grade durable plastic.

As shown in FIG. 3B, the hypotube 44 has an inner diameter that is sized to support a collet 50. The collet 50 has a cylindrically-shaped proximal portion 50A that is received inside the hypotube 44, abutting a step 44C. The collet 50 also has tapered cam fingers 50B that extends distally and downwardly toward the longitudinal axis of the ablation head 16. The collet cam fingers 50B reside inside the hypotube spring 46, 46A (FIG. 6) and radially align with the previously described strain-sensing FBGs 40, but not the temperature-sensing FBG 42, of the two, three or more optical fibers 38.

FIGS. 3B to 3D further show that a cylindrically-shaped collar 52 is received inside the distal portion 44B of the hypotube 44. The collar 52 has a proximal cam surface 52A that overlaps the tapered cam fingers 50B of the collet 50. With the ablation catheter 10 in an unarticulated orientation as shown in the solid lines in FIG. 1, the proximal cam surface 52A contacts an outer surface of the collet cam fingers 50B (FIGS. 2 and 3D). This contact location is radially aligned with the hypotube spring 46, 46A. In turn, the collect cam fingers 50B of the collet 50 rest against an outer surface of the strain-sensing FBGs 40 of the two, three or more optical fiber 38 in a neutral orientation, not imparting any strain on the FBGs 40. An annular ring 54 of epoxy secures the proximal portion 50A of the collet 50 inside the hypotube 44 abutting the inner hypotube step 44C. Suitable materials for the collet 50 and the collar 52 include stainless steel, nickel titanium, platinum, platinum iridium, and a medical grade durable plastic.

In the selectively manipulatable embodiment of the ablation catheter 10, in addition to the delivery lumen 18, the catheter body 12 has a number of push-pull wire lumens 56 extending from the catheter proximal portion 12A (FIG. 1) received in the handle assembly 14 to the distal catheter portion 12B. As previously described, in an exemplary system having four push-pull wires 34 anchored at evenly spaced 90° intervals about the circumference of the ablation head 16, there is a corresponding number of push-pull wire lumens 56 evenly spaced at 90° intervals in the sidewall of the catheter body 12.

A power cable lumen 57 is also depicted in FIGS. 2, 3A, 3C and 3D. The power cable 35 extends through this lumen 57.

Further, the catheter body 12 has a number of optical fiber lumens 58 extending from the catheter proximal portion 12 received in the handle assembly 14 to the distal catheter portion 12B. In an exemplary embodiment of the present ablation catheter 10 having three optical fibers 38 spaced at 120° intervals about the circumference of the ablation head 16, there is a corresponding number of optical fiber lumens 58 evenly spaced at 120° intervals in the sidewall of the catheter body 12. Each of the three optical fibers 38 has a corresponding strain-sensing FBG 40. As previously described, the plurality of strain-sensing FBGs 40 are radially aligned with the collet 50/collar 52 and the coil spring 46 of the hypotube 44. However, it is not necessary that each optical fiber 38 has both a strain-sensing FBG 40 and a temperature-sensing FBG 42. It is sufficient that there is only one temperature-sensing FBG 42 whose primary function is to compensate for the effect of temperature on the plurality of strain-sensing FBGs 40 in the vasculature environment immediately adjacent to the ablation head 16. While the strain-sensing FBGs 40 are responsive to temperature, the temperature-sensing FBG 42 is not responsive to strain.

Temperature information from the temperature-sensing FBG 42 is also useful is assessing the amount of heat being generated by the ablation head 16. This helps in regulating formation of an individual ablation at a tissue site.

A fiber Bragg grating (FBG) is a periodic modulation of the refractive index along the core of the optical fiber 38. The periodicity results in reflection of light waves that match the periodic spacing of the FBG wavelength while other wavelengths are transmitted unperturbed. The wavelength that is reflected by the FBG is determined by the "effective refractive index" of the grating in the fiber core and the period of the grating.

A FBG in a single mode optical fiber will reflect light waves of a wavelength centered around a single wavelength (a Bragg wavelength) as determined by the effective refractive index and the period of the grating. By altering these elements (the effective refractive index and the period of the grating), it is possible to configure the present optical fiber system comprising the exemplary two, three or more optical fibers, each having a respective strain-sensing FBG 40, to reflect light around two, three or more different wavelengths.

FIG. 4 illustrates an embodiment with three optical fibers, each having a dedicated broadband light source. More specifically, optical fiber 38A is optically connected to a first broadband light source 60A, optical fiber 38B is optically connected to a second broadband light source 60B, and optical fiber 38C is optically connected to a third broadband light source 60C. Any one of the three optical fibers, for example optical fiber 38C, is also optically connected to a fourth broadband light source 60D.

In another embodiment, there is only one broadband light source that selectively emits light into each optical fiber.

Light of a first spectrum from the first light source 60A is transmitted through a first circulator 62A and emitted into optical fiber 38A and then its strain-sensing FBG 40A (FIG. 6). The first spectrum covers all possible reflection spectrum from the strain-sensing FBG due to strain and temperature variations imparted to the FBG 40A. Similarly, light of a second spectrum from the second light source 60B is transmitted through a second circulator 62B and emitted into optical fiber 38B and then its strain-sensing FBG 40B. The second spectrum covers all possible reflection spectrum from the strain-sensing FBG due to strain and temperature variations imparted to the FBG 40B. And, light of a third spectrum from the third light source 60C is transmitted through a third circulator 62C and emitted into optical fiber 38C and then its strain-sensing FBG 40C. The third spectrum covers all possible reflection spectrum from the strain-sensing FBG due to strain and temperature variations imparted to the FBG 40C. Finally, light of a fourth spectrum from the fourth light source 60D is transmitted through the third circulator 62C and emitted into the third optical fiber 38C and then its temperature-sensing FBG 42. The fourth spectrum covers all possible reflection spectrum from the temperature-sensing FBG due to temperature variations imparted to the FBG 40D.

Figure 5A:
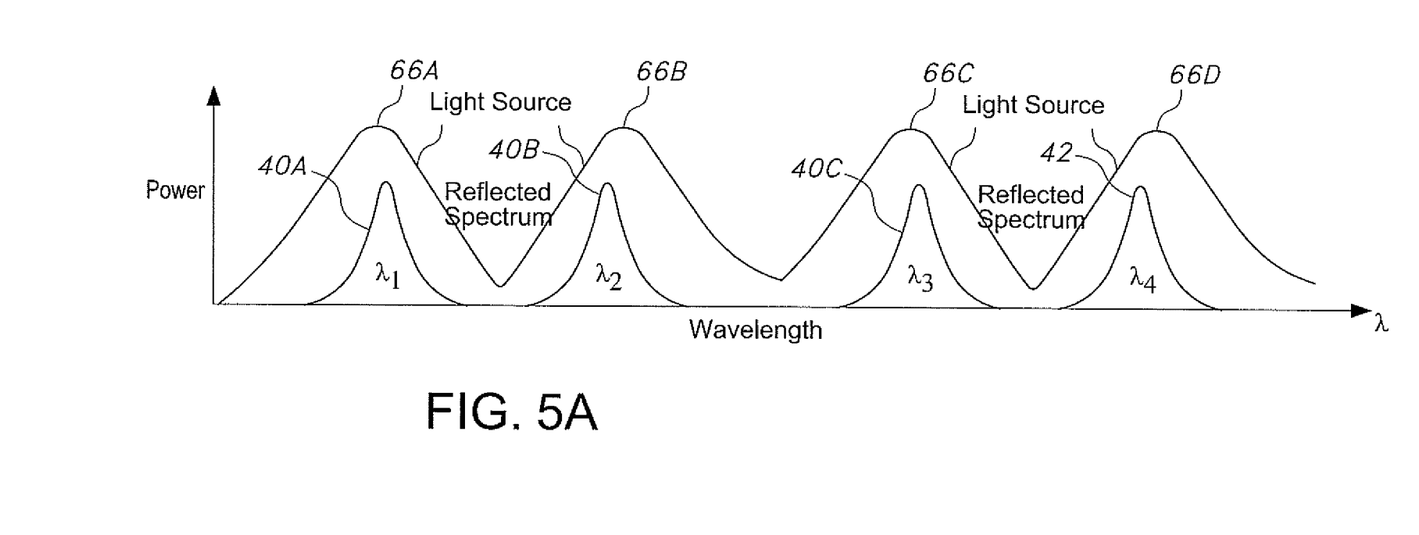
FIG. 5A is a graph depicting a three-optical fiber system with dedicated light sources 66A, 66B, 66C and 66D, each emitting light at a spectrum that covers all possible reflection spectrum from the respective strain-sensing FBGs 40A, 40B and 40C due to strain and temperature variations imparted to the strain-sensing FBGs and from the temperature-sensing FBG due to temperature variations imparted to the FBG 42.

As depicted in FIG. 5A, in a three-optical fiber system with dedicated light sources 66A, 66B, 66C and 66D, the light sources 60A to 60D each emit light at a spectrum that covers all possible reflection spectrum from the respective strain-sensing FBGs 40A, 40B and 40C due to strain and temperature variations imparted to the strain-sensing FBGs and the temperature-sensing FBG due to temperature variations imparted to the temperature-sensing FBG 42. If the strain-sensing FBGs 40A, 40B and 40C and the temperature-sensing FBG 42 reflect light of different Bragg wavelengths, the reflected light has respective peaks at $\lambda_1$, $\lambda_2$, $\lambda_3$ and $\lambda_4$. A narrow linewidth laser is suitable for the dedicated light sources 66A, 66B, 66C and 66D.

Figure 5B:
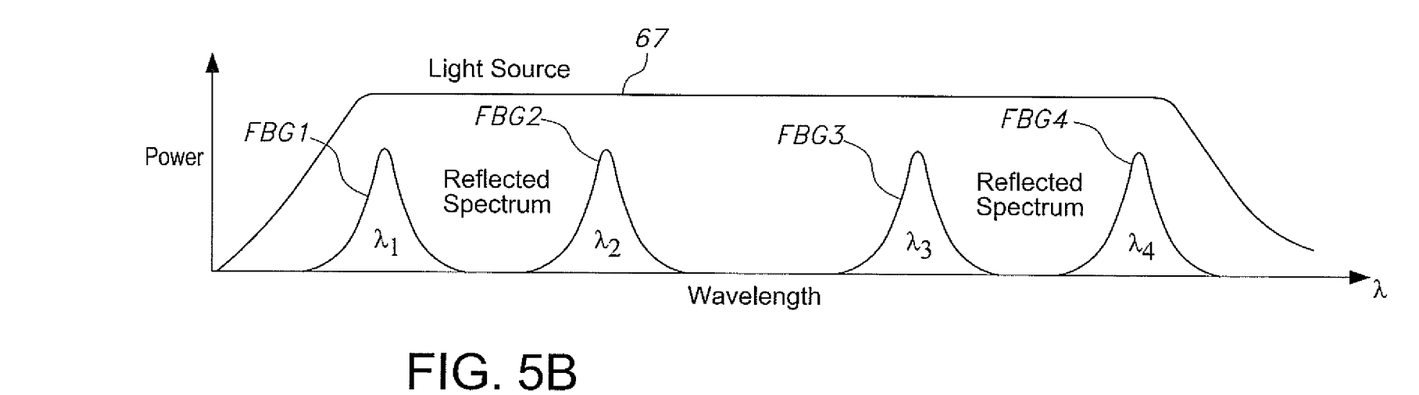
FIG. 5B is a graph depicting a three-optical fiber system using one broadband light sources 67 that emits light at a spectrum that covers all possible reflection spectrum from the respective strain-sensing FBGs 40A, 40B and 40C due to strain and temperature variations imparted to the strain-sensing FBGs and the temperature-sensing FBG due to temperature variations imparted to the temperature-sensing FBG 42.

FIG. 5B depicts a three-optical fiber system using one broadband light sources 67 that emits light at a spectrum covering all possible reflection spectrum from the respective strain-sensing FBGs 40A, 40B and 40C due to strain and temperature variations imparted to the strain-sensing FBGs and the temperature-sensing FBG due to temperature variations imparted to the temperature-sensing FBG 42. If the strain-sensing FBGs 40A, 40B and 40C and the temperature-sensing FBG 42 reflect light of different Bragg wavelengths, the reflected light has respective peaks at $\lambda_1$, $X_2$, $\lambda_3$ and $\lambda_4$. A Superluminescent Light Emitting Diode (SLED) or a scanning laser is a suitable broadband light source.

In either the dedicated light source embodiment or the broadband light source embodiment, light reflected by the FBGs 40A to 40C and 42 returns via their respective circulator 62A, 62B and 62C into a corresponding wavelength detector 64A, 64B, 64C and 64D. Each detector analyzes the light it receives to identify the intensity of the light at various wavelengths. This information is forwarded to a controller 70 having a visual display 72. Among other useful information, the controller 70 is programmed to calculate the precise orientation of the ablation head 16 in the vasculature and the force that the head is exerting against myocardial tissue. The display 72 presents this information in real-time in any one of a variety of formats that are useful to the physician.

Because the temperature at any location in the vasculature impacts the temperature-sensing FBG 42 in the same manner as it impacts the strain-sensing FBGs 40A, 40B and 40C, wavelength shifts due to temperature are substantially identical at the three strain-sensing FBGs. As a result, movement of wavelength peak $\lambda_4$ in FIGS. 5A and 5B of the temperature-sensing FBG 42 is used by the controller 70 to calculate the extent to which the wavelength peaks of the strain-sensing FBGs 40A, 40B and 40C are moved because of a change in temperature. Thus, wavelength shifts in the light received from the temperature-sensing FBG 42 cancel out the effect of temperature change on the strain-sensing FBGs 40A, 40B and 40C. Any movement in the wavelength peaks of the strain-sensing FBGs 40A, 40B and 40C beyond that expected because of a temperature change is indicative of strain from the collet cam fingers 50B contacting the optical fibers 38A to 38C at the respective strain-sensing FBGs 40A, 40B and 40C. Movement of the wavelength peaks due to pressure or strain detected at each of the three strain-sensing FBGs 40A, 40B and 40C is then converted by the controller 70 into a value related to the force that the ablation head 16 is exerting against myocardial tissue.

In the selectively manipulatable embodiment of the ablation catheter 10, the orientation of the ablation head 16 caused by manipulation of the push-pull wires 34 is first ascertained by the controller 70 and then when the ablation head is pressed against myocardial tissue, any added change in the reflected Bragg wavelengths is used by the controller to calculate the additional force vector resulting from contact with myocardial tissue.

In Use

In what is referred to as a transseptal approach in an exemplary cardiac ablation therapy to correct for atrial arrhythmia, an introducer sheath is introduced through a peripheral vein (typically a femoral vein) and advanced into the right atrium of a patient's cardiac muscle. After the introducer sheath is used to make an incision in the fossa ovalis (the tissue wall between the left and right atriums), the introducer is moved through the incision and anchored in the fossa ovalis. Next, the ablation catheter 10 is steered or guided through the left atrium to orient the ablation head 16 in a desired location within the left atrium, such as in proximity to a pulmonary vein where an ablation therapy is to be applied.

In an embodiment without push-pull wires, the physician advances the catheter body 12 and its distal ablation head 16 toward a target myocardial site under fluoroscopy-guided observation. In an alternate embodiment with push-pull wires 44, the physician manipulates the handle assembly 14 to selectively tension and relax the push-pull wires 34 to control the orientation of the distal ablation head 16 as it is advanced under fluoroscopy-guided observation toward a target myocardial site.

With the ablation head 16 in a neutral, unarticulated orientation as shown in the solid lines in FIG. 1, the proximal collar cam surface 52A applies an equal annular force to the tapered cam fingers 50B of the collet 50. The collect cam fingers 50B in turn apply an equal annular force to each of the three strain-sensing FBGs 40A, 40B and 40C.

Thus, with the dedicated light sources 66A, 66B and 66C or the broadband light source 67 emitting the first light spectrum into the first strain-sensing FBG 40A, the second light spectrum into the second strain-sensing FBG 40B, the third light spectrum into the third strain-sensing FBG 40C and the fourth light spectrum into the fourth temperature-sensing FBG, in comparison to a first state of the reflected first, second and third Bragg wavelengths with no axial force imparted to the ablation head 16, with an axial force imparted to the ablation head to cause the ablation head to assume a neutral, unarticulated orientation axially aligned with the catheter body 12, the collar/collet 52/50 assembly applies equal radial pressure to the first, second and third strain-sensing FBGs. The reflected first, second and third Bragg wavelengths $\lambda_1$, $\lambda_2$ and $\lambda_3$ received by the respective first, second and third wavelength detectors 64A, 64B and 64C are in a second state, shifted a similar amount with respect to the first state.

The controller 70 is programmed to calculate a temperature induced shifted first, second and third Bragg wavelength as the difference between a first state of the reflected fourth Bragg wavelength $\lambda_4$ of the fourth temperature-sensing FBG 42 at a first ambient temperature with the ablation head 16 outside a body tissue in comparison to a second state of the reflected fourth Bragg wavelength of the fourth FBG 42 at a second, local environment temperature with the ablation head 16 inside a body tissue. The controller 70 is programmed to thereby indicate a temperature-compensated magnitude of the axial force vector imparted to the ablation head 16.

As the physician advances the ablation head 16 through the vasculature to the myocardial site of interest, whether through manipulation of the handle 14 to steer the push-pull wires 34, or not, one of more of the push-pull wires 44 is put under tension while the other wires are relaxed. The degree to which tension on any one of the plurality of push-pull wires is increased or relaxed is precisely monitored by measuring the reflected Bragg wavelength of the reflected light from each of the strain-sensing FBGs 40A, 40B and 40C. That is as the ablation head 16 flexes or bends at the hypotube spring 46 to assume an articulated orientation (depicted in dashed lines in FIG. 1), the collar 52 is moved out of alignment with the aligned axes of the catheter body 12 and its ablation head 16. As the ablation head 16 moves into an articulated orientation, out of axial alignment with the catheter body 12, the proximal cam surface 52A of the collar 52 applies a lateral force against the tapered cam fingers 50B of the collet 50 so that the cam fingers press against one of the strain-sensing FBGs 40A, 40B and 40C with a greater force than against the other strain-sensing FBGs. The relative lateral force or strain imparted to each FBG 40A, 40B and 40C changes the reflected Bragg wavelength from the strain-sensing FBGs 40A, 40B and 40C. The altered Bragg wavelength of the reflected light from each FBG 40A, 40B and 40C is measured by their respective wavelength detector 64A, 64B and 64C and sent to the controller 70 for processing into useful information.

In that respect, when a lateral force is imparted to the ablation head to cause the ablation head 16 to deflect out of axial alignment with the catheter body 12, the spring 46, 46A of the hypotube 44 deflects out of axial alignment to cause the collar/collet assembly 52/50 to apply a first lateral force to the first strain-sensing FBG 40A, a second lateral force to the second strain-sensing FBG 40B and a third lateral force to the third strain-sensing FBG 40C. In comparison to the first state of the reflected first, second and third Bragg wavelengths, a lateral force induced reflected first Bragg wavelength of the first strain-sensing FBG is in a second state, shifted the same as or a different amount than a lateral force induced reflected second Bragg wavelength of the second FBG in a third state, shifted the same as or a different amount than a lateral force induced reflected third Bragg wavelength of the third FBG in a fourth state. The controller 70 is programmed to compensate for the effect of the temperature induced shifted fourth Bragg wavelength on the reflected first, second and third Bragg wavelengths in the axial force induced second, third and fourth states to thereby indicate a temperature-compensated magnitude of the axial force vector imparted to the ablation head 16.

The controller 70 is further programmed to compensate for the effect of the temperature induced shifted fourth Bragg wavelength on the reflected first, second and third Bragg wavelengths in the respective lateral force induced second, third, and fourth states to thereby indicate a temperature-compensated lateral force vector imparted to the ablation head 16 as a result of the collar/collet assembly 52/50 applying the first lateral force to the first strain-sensing FBG, the second lateral force to the second strain-sensing FBG, and the third lateral force to the strain-sensing third FBG.

Thus, the controller 70 is programmed to detect and analyze the received Bragg wavelengths and, after compensating for the temperature-associated Bragg wavelength shift detected in the temperature-sensing FBG 42, output the precise orientation of the ablation head 16 in the vasculature on the display 72. In addition to calculating the orientation of the ablation head 16, the controller 70 is also programmed to analyze the detected Bragg wavelengths, compensate for temperature-associated Bragg wavelength shift, and output a precise reading related to the force that the ablation head 16 is exerting against myocardial tissue, and the like, during a diagnostic or therapeutic medical procedure, such as a cardiac ablation.

As previously discussed, ablation therapies are used to make many individual ablations in a controlled fashion in order to form a lesion line. To improve conformity of the lesion line, precise orientational control of the catheter 10 and its ablation head 16 when the individual ablations are conducted is desired. This means that the contact force between the ablation head 16 and the targeted tissue, and the ablation period are important. After a controlled therapy application, necrosis of the targeted tissue along the lesion line increases the resistance of the pulmonary vein to the flow of electrical signals through the pulmonary vein to the cardiac muscle. Thus, the ablation catheter 10 of the present invention represents an advance in the delivery of diagnostic and therapeutic medical procedures to diagnose and treat a wide variety of medical conditions such as atrial arrhythmia, including for example, ectopic atrial tachycardia, atrial fibrillation, and atrial flutter.

It is appreciated that various modifications to the inventive concepts described herein may be apparent to those of ordinary skill in the art without departing from the spirit and scope of the present invention as defined by the appended claims.

What is claimed is:

1. An ablation catheter, comprising:
    a) a flexible, elongate catheter body extending from a catheter body proximal end to a catheter body distal end;
    b) an ablation head configured to electrically conduct at least one of a direct current energy and a radio-frequency energy into a target tissue;
    c) a power cable supported by the catheter body, the power cable being connectable to a power source for electrically energizing the ablation head;
    d) a hypotube disposed between and connected to the catheter body distal end and to the ablation head, wherein the hypotube comprises a spring;
    e) at least a first optical fiber and a second optical fiber, both the first and second optical fibers extending from the catheter body proximal end to the hypotube, wherein the first optical fiber comprises a first strain-sensing fiber Bragg grating (FBG) having a first Bragg wavelength, and the second optical fiber comprises a second strain-sensing FBG having a second Bragg wavelength;
    f) a collar/collet assembly radially aligned with the spring of the hypotube and the first and second strain-sensing FBGs;
    g) at least one light source optically connected to the first and second optical fibers, wherein the light source is configured to emit light of a first spectrum into the first strain-sensing FBG and emit light of a second spectrum into the second strain-sensing FBG;
    h) a first light wavelength detector optically connected to the first FBG of the first optical fiber and a second light wavelength detector optically connected to the second FBG of the second optical fiber; and
    i) a controller operatively coupled to the first and second light wavelength detectors,
    j) wherein, with the at least one light source emitting the first light spectrum into the first FBG and the second light spectrum into the second FBG, and wherein, in comparison to a first state of the reflected first and second Bragg wavelengths with no axial or lateral force imparted to the ablation head, with only an axial force imparted to the ablation head to cause the spring to compress but with the ablation head remaining axially aligned with the catheter body, the collar/collet assembly applies equal radial force to the first and second strain-sensing FBGs so that the first and second light wavelength detectors receive the reflected first and second Bragg wavelengths in a second state, shifted the same amount with respect to the first state of the reflected first and second Bragg wavelengths, and wherein the controller is programmed to calculate the difference between the first and second states of the reflected first and second Bragg wavelengths and to convert the difference into the magnitude of the axial force vector imparted to the ablation head, and k) wherein, with both axial and lateral forces imparted to the ablation head to cause the ablation head to deflect out of axial alignment with the catheter body, the spring of the hypotube compresses and deflects out of axial alignment to cause the collar/collet assembly to apply a greater lateral force to the first FBG than to the second FBG so that in comparison to the first state of the reflected first and second Bragg wavelengths, a lateral-force-induced third state of the reflected first Bragg wavelength is shifted a greater amount than a lateral-force-induced fourth state of the reflected second Bragg wavelength, and wherein the controller is programmed to calculate the difference in the lateral-force-induced third and fourth states of the reflected first and second Bragg wavelengths in comparison to the first state of the reflected first and second Bragg wavelengths and to convert the difference into a lateral force magnitude and vector imparted to the ablation head.

2. The ablation catheter of claim 1, wherein:
a) the first optical fiber also comprises a third temperature-sensing FBG having a third Bragg wavelength;
b) the at least one light source optically connected to the first optical fiber is configured to emit light of a third spectrum into the third temperature-sensing FBG; and
c) a third light wavelength detector is optically connected to the third FBG of the first optical fiber, and
d) with the at least one light source emitting the third light spectrum into the third FBG, the controller is operably coupled to the third light wavelength detector and programmed to calculate a temperature-induced third Bragg wavelength shift as the difference between a fifth state of the reflected third Bragg wavelength at a first ambient temperature with the ablation head outside a body tissue in comparison to a sixth state of the reflected third Bragg wavelength at a second, local environment temperature with the ablation head inside a body tissue, and
e) wherein the controller is further programmed to calculate for:
i) the effect of the temperature change on the reflected first and second Bragg wavelengths in the axial-force-induced second state from the temperature-induced third Bragg wavelength shift to thereby calculate a temperature-compensated magnitude of the axial force vector imparted to the ablation head, and
ii) the effect of the temperature change on the reflected first and second Bragg wavelengths in the respective lateral-force-induced third and fourth states from the temperature-induced third Bragg wavelength shift to thereby calculate a temperature-compensated lateral force magnitude and vector imparted to the ablation head as a result of the collar/collet assembly applying a greater lateral force to the first FBG than to the second FBG.

3. The ablation catheter of claim 2, wherein the first FBG, the second FBG and the third FBG are individually selected from the group of a phase-shifted FBG, a long-period FBG, an apodized FBG, a chirped FBG, and a tilted FBG.

4. The ablation catheter of claim 2, further comprising:
a) a third optical fiber extending from the catheter body proximal end to the hypotube, the third optical fiber comprising a fourth strain-sensing FBG having a fourth Bragg wavelength, wherein the collar/collet assembly is radially aligned with the spring of the hypotube and the first, second and fourth strain-sensing FBGs, and wherein the at least one light source is optically connected to the third optical fiber, the light source being configured to emit light of a fourth spectrum into the fourth strain-sensing FBG, and
b) a fourth light wavelength detector optically connected to the fourth FBG of the third optical fiber, and
c) wherein, with the at least one light source emitting the first light spectrum into the first FBG, the second light spectrum into the second FBG, and the fourth light spectrum into the fourth FBG, and wherein, in comparison to a first state of the reflected first, second and fourth Bragg wavelengths with no axial or lateral force imparted to the ablation head, with only an axial force imparted to the ablation head to cause the spring to compress but with the ablation head remaining axially aligned with the catheter body, the collar/collet assembly applies equal radial force to the first, second and fourth strain-sensing FBGs so that the first, second and fourth light wavelength detectors receive the reflected first, second and fourth Bragg wavelengths in a second state, shifted the same amount with respect to the first state of the reflected first, second and fourth Bragg wavelengths, and wherein the controller is also operatively coupled to the fourth light wavelength detector and programmed to calculate the difference between the first and second states of the reflected first, second and fourth Bragg wavelengths and to convert the difference into the magnitude of the axial force vector imparted to the ablation head, and
d) wherein, with both axial and lateral forces imparted to the ablation head to cause the ablation head to deflect out of axial alignment with the catheter body, the spring of the hypotube compresses and deflects out of axial alignment to cause the collar/collet assembly to apply a first lateral force to the first FBG, a second lateral force to the second FBG and a third lateral force to the fourth FBG so that in comparison to the first state of the reflected first, second and fourth Bragg wavelengths, the lateral-force-induced third state of the reflected first Bragg wavelength is shifted the same as or a different amount than the lateral-force-induced fourth state of the reflected second Bragg wavelength, shifted a different amount than a lateral-force-induced seventh state of the reflected fourth Bragg wavelength, and wherein the controller is programmed to calculate the differences in the lateral-force-induced third, fourth and seventh states of the reflected first, second and fourth Bragg wavelengths in comparison to the first state of the reflected first, second and fourth Bragg wavelengths and to convert the difference into a lateral force magnitude and vector imparted to the ablation head.

5. The ablation catheter of claim 4, wherein the first, second and third optical fibers are evenly spaced at 120° intervals about a circumference of the ablation head.

6. The ablation catheter of claim 1, wherein the catheter body includes a delivery lumen that extends to the catheter body distal end, and wherein the ablation head has an ablation head lumen in open communication with the hypotube and the catheter body delivery lumen.

7. The ablation catheter of claim 1, wherein the first and second optical fibers are connected to the ablation head.

8. The ablation catheter of claim 1, wherein the first and second optical fibers are diametrically opposed to each other inside the hypotube.

9. The ablation catheter of claim 1, wherein a handle assembly is connected to the proximal end of the catheter body, and wherein at least one push-pull wire extends from the handle assembly to the ablation head, and wherein the handle assembly is manipulatable to move the at least one push-pull wire to selectively deflect the ablation head out of axial alignment with the catheter body.

10. The ablation catheter of claim 9, wherein there are four push-pull wires extending from the handle assembly to the ablation head, the four push-pull wires being evenly spaced at 90° intervals about a circumference of the ablation head.

11. The ablation catheter of claim 1, wherein the at least one light source is selected from a Superluminescent Light Emitting Diode (SLED) and a scanning laser.

12. The ablation catheter of claim 1, wherein a first light source is optically connected to the first optical fiber and a second light source is optically connected to the second optical fiber.

13. The ablation catheter of claim 12, wherein the first and second light sources are narrow linewidth lasers.

14. The ablation catheter of claim 1, wherein the hypotube comprises a coil spring or a slotted spring.

15. The ablation catheter of claim 1, wherein, in addition to being configured to electrically conduct at least one of a direct current energy and a radio-frequency energy into a target tissue, the ablation head is also configured for at least one of cryoablation, laser ablation, chemical ablation, and ultrasonic ablation of a target tissue.

16. An ablation catheter, comprising:
a) a flexible, elongate catheter body extending from a catheter body proximal end to a catheter body distal end;
b) an ablation head configured to electrically conduct at least one of a direct current energy and a radio-frequency energy into a target tissue;
c) a power cable supported by the catheter body, the power cable being connectable to a power source for electrically energizing the ablation head;
d) a hypotube disposed between and connected to the catheter body distal end and to the ablation head, wherein the hypotube comprises a spring;
e) at least a first optical fiber, a second optical fiber and a third optical fiber, the first, second and third optical fibers extending from the catheter body proximal end to the hypotube, wherein the first optical fiber comprises a first strain-sensing fiber Bragg grating (FBG) having a first Bragg wavelength, the second optical fiber comprises a second strain-sensing FBG having a second Bragg wavelength, and the third optical fiber comprises a third strain-sensing FBG having a third Bragg wavelength, and wherein the first optical fiber further comprises a fourth temperature-sensing FBG having a fourth Bragg wavelength;
f) a collar/collet assembly radially aligned with the spring of the hypotube and the first, second and third strain-sensing FBGs;
g) at least one light source optically connected to the first, second and third optical fibers, wherein the light source is configured to emit light of a first spectrum into the first strain-sensing FBG, emit light of a second spectrum into the second strain-sensing FBG, emit light of a third spectrum into the third strain-sensing FBG, and emit light of a fourth spectrum into the fourth temperature-sensing FBG;
h) a first light wavelength detector optically connected to the first FBG of the first optical fiber, a second light wavelength detector optically connected to the second FBG of the second optical fiber, a third light wavelength detector optically connected to the third FBG of the third optical fiber, and a fourth light wavelength detector optically connected to the fourth FBG of the first optical fiber; and
i) a controller operatively coupled to the first, second, third and fourth light wavelength detectors,
j) wherein, with the at least one light source emitting the first light spectrum into the first FBG, the second light spectrum into the second FBG, the third light spectrum into the third FBG, and the fourth light spectrum into the fourth FBG, and wherein, in comparison to a first state of the reflected first, second and third Bragg wavelengths with no axial or lateral force imparted to the ablation head, with only an axial force imparted to the ablation head to cause the spring to compress but with the ablation head remaining axially aligned with the catheter body, the collar/collet assembly applies equal radial force to the first, second and third strain-sensing FBGs so that the first, second and third light wavelength detectors receive the reflected first, second and third Bragg wavelengths in a second state, shifted the same amount with respect to the first state of the reflected first, second and third Bragg wavelengths, and
k) wherein the controller is programmed to calculate a temperature-induced fourth Bragg wavelength shift as the difference between a third state of the reflected fourth Bragg wavelength of the fourth FBG at a first ambient temperature with the ablation head outside a body tissue in comparison to a fourth state of the reflected fourth Bragg wavelength of the fourth FBG at a second, local environment temperature with the ablation head inside a body tissue, and
l) wherein the controller is programmed to calculate for the effect of the temperature change on the reflected first, second and third Bragg wavelengths in the axial-force-induced second state from the temperature-induced fourth Bragg wavelength shift to thereby calculate a temperature-compensated magnitude of the axial force vector imparted to the ablation head, and
m) wherein, with both axial and lateral forces imparted to the ablation head to cause the ablation head to deflect out of axial alignment with the catheter body, the spring of the hypotube compresses and deflects out of axial alignment to cause the collar/collet assembly to apply a first lateral force to the first FBG, a second lateral force to the second FBG and a third lateral force to the third FBG so that in comparison to the first state of the reflected first, second and third Bragg wavelengths, a lateral-force-induced fifth state of the reflected first Bragg wavelength is shifted the same as or a different amount than a lateral-force-induced sixth state of the reflected second Bragg wavelength, shifted a different amount than a lateral-force-induced seventh state of the reflected third Bragg wavelength, and
n) wherein the controller is further programmed to calculate for the effect of the temperature change on the reflected first, second and third Bragg wavelengths in the respective lateral-force-induced fifth, sixth, and seventh states from the temperature-induced fourth Bragg wavelength shift to thereby calculate a temperature-compensated lateral force magnitude and vector imparted to the ablation head as a result of the collar/collet assembly applying the first lateral force to the first FBG, the second lateral force to the second FBG and the third lateral force to the third FBG.

17. The ablation catheter of claim 16, wherein, in addition to being configured to electrically conduct at least one of a direct current energy and a radio-frequency energy into a target tissue, the ablation head is also configured for at least one of cryoablation, laser ablation, chemical ablation, and ultrasonic ablation of a target tissue.

18. An ablation catheter, comprising:
 a) a flexible, elongate catheter body extending from a catheter body proximal end to a catheter body distal end;
 b) an ablation head configured to electrically conduct at least one of a direct current energy and a radio-frequency energy into a target tissue;
 c) a power cable supported by the catheter body, the power cable being connectable to a power source for electrically energizing the ablation head;
 d) a hypotube disposed between and connected to the catheter body distal end and to the ablation head, wherein the hypotube comprises a spring;
 e) a handle assembly connected to the proximal end of the catheter body;
 f) at least one push-pull wire extending from the handle assembly connected to the proximal end of the catheter body to the ablation head;
 g) at least a first optical fiber and a second optical fiber, both the first and second optical fibers extending at least from the catheter body proximal end to the hypotube, wherein the first optical fiber comprises a first strain-sensing fiber Bragg grating (FBG) having a first Bragg wavelength, the second optical fiber comprises a second strain-sensing FBG having a second Bragg wavelength, and the first optical fiber also comprises a third temperature-sensing FBG having a third Bragg wavelength;
 h) a collar/collet assembly radially aligned with the spring of the hypotube and the first and second strain-sensing FBGs;
 i) at least one light source optically connected to the first and second optical fibers, wherein the light source is configured to emit light of a first spectrum into the first strain-sensing FBG, emit light of a second spectrum into the second strain-sensing FBG, and emit light of a third spectrum into the third temperature-sensing FBG;
 j) a first light wavelength detector optically connected to the first FBG of the first optical fiber, a second light wavelength detector optically connected to the second FBG of the second optical fiber, and a third light wavelength detector optically connected to the third FBG of the first optical fiber; and
 k) a controller operatively coupled to the first, second and third light wavelength detectors,
 l) wherein, with the at least one light source emitting the first light spectrum into the first FBG, the second light spectrum into the second FBG, and the third light spectrum into the third FBG, and wherein, in comparison to a first state of the reflected first and second Bragg wavelengths with no axial or lateral forces imparted to the ablation head, with only an axial force imparted to the ablation head to cause the spring to compress but with the ablation head remaining axially aligned with the catheter body, the collar/collet assembly applies equal radial force to the first and second strain-sensing FBGs so that the first and second light wavelength detectors receive the reflected first and second Bragg wavelengths in a second state, shifted the same amount with respect to the first state of the reflected first and second Bragg wavelengths, and wherein the controller is programmed to calculate the difference between the first and second states of the reflected first and second Bragg wavelengths and to convert the difference into the magnitude of the axial force vector imparted to the ablation head, and
 m) wherein the handle assembly is manipulatable to move the at least one push-pull wire to selectively deflect the ablation head out of axial alignment with the catheter body, and wherein such movement causes the spring of the hypotube to compress and deflect out of axial alignment to cause the collar/collet assembly to apply a greater lateral force to the first FBG than to the second FBG so that in comparison to the first state of the reflected first and second Bragg wavelengths, a lateral-force-induced third state of the reflected first Bragg wavelength is shifted a greater amount than a lateral-force-induced fourth state of the reflected second Bragg wavelength, and wherein the controller is programmed to calculate the difference in the lateral-force-induced third and fourth states of the reflected first and second Bragg wavelengths in comparison to the first state of the reflected first and second Bragg wavelengths and to convert that difference into a lateral force magnitude and vector imparted to the ablation head, and
 n) wherein the controller is further programmed to:
  i) calculate a temperature-induced third Bragg wavelength shift as the difference between a fifth state of the reflected third Bragg wavelength at a first ambient temperature with the ablation head outside a body tissue in comparison to a sixth state of the reflected third Bragg wavelength at a second, local environment temperature with the ablation head inside a body tissue, and
  ii) calculate for the effect of the temperature change on the reflected first and second Bragg wavelengths in the axial-force-induced second state from the temperature-induced third Bragg wavelength shift to thereby calculate a temperature-compensated magnitude of the axial force vector imparted to the ablation head, and
  iii) calculate for the effect of the temperature change on the reflected first and second Bragg wavelengths in the respective lateral-force-induced third and fourth states from the temperature-induced third Bragg wavelength shift to thereby calculate a temperature-compensated lateral force magnitude and vector imparted to the ablation head as a result of the collar/collet assembly applying a greater lateral force to the first FBG than to the second FBG.

19. The ablation catheter of claim 18, wherein, in addition to being configured to electrically conduct at least one of a direct current energy and a radio-frequency energy into a target tissue, the ablation head is also configured for at least one of cryoablation, laser ablation, chemical ablation, and ultrasonic ablation of a target tissue.

* * * * *